(12) United States Patent
Gurton (10) Patent No.: US 7,304,742 B1
(45) Date of Patent: Dec. 4, 2007

(54) FLOW-THROUGH AEROSOL PHOTOACOUSTIC SYSTEMS AND METHODS

(75) Inventor: Kristan P. Gurton, Olney, MD (US)

(73) Assignee: United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/246,291

(22) Filed: Oct. 11, 2005

Related U.S. Application Data

(60) Provisional application No. 60/617,406, filed on Oct. 9, 2004.

(51) Int. Cl.
*G01N 21/00* (2006.01)

(52) U.S. Cl. ........................ 356/432; 356/437; 356/438

(58) Field of Classification Search ................ 356/432
See application file for complete search history.

(56) References Cited

U.S. PATENT DOCUMENTS

| | | | | |
|---|---|---|---|---|
| 4,187,026 A * | 2/1980 | Schaffer et al. | ............. | 356/326 |
| 6,408,681 B1 * | 6/2002 | Gurton et al. | ............. | 73/24.02 |

* cited by examiner

*Primary Examiner*—Roy M. Punnoose
(74) *Attorney, Agent, or Firm*—William W. Randolph; Richard A. Morgan

(57) ABSTRACT

Embodiments of photoacoustic devices, systems, and methods are disclosed. One device embodiment, among others, comprises a flow-through configuration for a test sample gas and a modular set of two or more solid-state or gaseous based lasers.

21 Claims, 6 Drawing Sheets

FIG. 1

Aerosol/
Acoustic
Flow in

A

B

A

B

A

6

Aerosol/
Acoustic
Flow out

FLOW-THROUGH AEROSOL PHOTOACOUSTIC SYSTEMS AND METHODS

CROSS-REFERENCE TO RELATED APPLICATION

This application is related to and claims the benefit of U.S. Provisional Patent Application No. 60/617,406 filed Oct. 9, 2004, the complete disclosure of which is incorporated herein by reference in its entirety.

GOVERNMENT INTEREST

The invention described herein can be manufactured, used, and licensed by or for the, United States Government without the payment of any royalties thereon.

BACKGROUND

1. Technical Field

The present disclosure is generally related to photoacoustic systems and methods and, more particularly, is related to aerosol photoacoustic systems and methods.

2. Description of the Related Art

Recent terrorist activities in the United States and elsewhere have demonstrated the susceptibility of both military and civilian personnel to chemical/biological aerosol attacks and the need to develop some type of early warning system. The majority of "point" sensors deployed in the field today fall into two basic categories: 1) chemical analysis on captured aerosol samples (very specific identification); and 2) an optical approach that relies on measuring the fluorescence phenomena inherent in most living things (very general discrimination). However, both approaches suffer from limitations. See J. Ho, "Real Time Detection of Biological Aerosols", Defense Research Establishment Suffield, *DRES R&D Bulletin* 96001; P. Hairston, J. Ho, F. R. Quant, "Design of an Instrument for Real-Time Detection of Bioaerosols using Simultaneous Measurement of Particle Aerodynamic Size and Intrinsic Fluorescence", *J. Aerosol Sci.* 28, no.3, 471, (1997).

Chemical methods that rely on various forms of antibody-tagging and/or chemical analysis often require periods on the order of several minutes in order for the chemical reaction to occur. In addition to the undesirable long periods of time needed to complete the analysis, these "wet chemistry" approaches generate quantities of toxic waste that require special handling and disposal.

Optical methods that are based on fluorescence operate in a more "real-time" manner; however, resultant measured fluorescent spectra is extremely sensitive to small quantities of contaminating media and/or particle morphology, resulting in false alarms. See G.W. Faris, R.A. Copeland, "Spectrally Resolved Absolute Fluorescence Cross Section of B. Globigii and B. Cereus", Stanford Research Institute, *Technical Report* 2913, (1992); B. Bronk, L. Reinisch, "Variability of steady-state bacterial fluorescence with respect to growth conditions", *Appl. Spectroscopy*, vol. 47, no. 4 pp. 436-440 (1993). When high-quality uncontaminated fluorescence spectra is recorded, it is often quite broad and featureless, making species discrimination and/or identification very difficult. See R. Pinnick, S. Hill, P. Nachman, "Aerosol fluorescence spectrum analyzer for rapid measurement of single micrometer-sized airborne biological particles", *Aerosol Science & Tech.*, vol. 28, no. 2, pp. 95-104, (1998).

A more desirable approach would be an optically based detection scheme that is sensitive enough to warn of the presence of a harmful airborne agent, but not so sensitive that it would result in many false positives, e.g., presence of residual growth media and changes in particle size or shape due to agglomeration.

Early development of aerosol photoacoustics was limited to single wavelength operation and, as a result, the method was thought to have little utility outside of the area of analytic spectroscopy. See C.W. Bruce, N.M. Richardson, "Propagation at 10 µm through smoke produced by atmospheric combustion of diesel fuel," *Appl. Opt.*, vol. 22, no. 7, pp. 1051-1056 (1983); C.W. Bruce, T.F. Stromberg, K.P. Gurton, "Trans-Spectral Absorption and Scattering of Electromagnetic Radiation by Diesel Soot," *Appl. Opt.*, vol. 30, no. 12, pp. 1537-1546 (1991). A brief description of the photoacoustic method is as follows.

Consider a sample volume containing a collection of optically absorbing particles, e.g., an aerosol. When a laser is passed through this volume a portion of the light will be absorbed by the aerosol particles, resulting in particle heating. Heat energy from the absorbing particle will transfer to the surrounding media and result in a pressure rise within the sample volume. If the laser is modulated at some convenient acoustic frequency, e.g., 1 kHz, a resultant acoustic signal will result at that same 1 kHz modulation frequency. This acoustic signal is then detected and amplified using a variety of means. It is established that the power of the resultant acoustic signal is directly proportional to the optical absorption cross-section of the absorbing particles. See A. Rosencwag, *Photoacoustics and Photoacoustic Spectroscopy*, Krieger Pub., New York (1990).

In principle, aerosol photoacoustics depends only on the fraction of light absorbed by the media and thus requires no a priori knowledge of aerosol particle shape, size, or complex refractive index. By designing a system in which the probe laser(s) also serve as a coincident short-pass transmissometer, an independent, absolute measure of the total extinction is also obtained. As a result, accurate values of the single-scatter albedo are also determined by taking the difference between the total extinction and absorption. See C. Bohren, D. Huffman, *Absorption and Scattering of Light by Small Particles*, Wiley-Interscience Press, New York, NY (1983).

Prior attempts at applying conventional photoacoustic spectroscopy to an aerosol media used a single monochromatic source and a "closed" sample volume geometry. See D.M. Roessler, F.R. Faxvog, "Optoacoustic measurement of optical absorption in acetylene smoke," *J. Opt. Soc. Am.*, vol. 69, no. 12, pp. 1699-1704, (1979). As a result, these methods were subject to problems associated with non-uniform aerosol concentrations due to, e.g., particle settling. In addition, these closed systems relied on optical windows to transmit the optical energy into the photoacoustic cell. Often, for moderately absorbing aerosols, the residual absorption due to the window substrate is comparable or greater than the absorption of the aerosol in question. See C.W. Bruce, R.G. Pinnick, "In-situ measurements of aerosol absorption with a resonate cw laser spectrophone," *AppL Opt.*, vol. 16, no. 7, pp. 1762-1765 (1977).

U.S. Patents relating to particle testing systems and methods include U.S. Pat. No. 6,694,799 issued to Small; U.S. Pat. No. 6,662,627 to Arnott et al.; U.S. Pat. No. 6,408,681 to Gurton et al.; U.S. Pat. No. 6,396,058 Gurton; U.S. Pat. No. 4,740,086 to Oehler et al.; U.S. Pat. No. 4,657,397 to Oehler et al.; U.S. Pat. No. 4,415,265 to Campillo et al.; and U.S. Pat. No. 4,187,026 to Schaffer et al., the teachings of each of which are fully incorporated herein by reference.

SUMMARY

Embodiments of photoacoustic devices, systems, and methods are disclosed. One method embodiment, among others, comprises determining an infrared (IR) absorption spectra of the chemical/biological agent of interest; modulating at least two lasers in a photoacoustic device, each modulated laser operating at one of at least two identified wavelengths from the IR spectra; introducing a test sample into the photoacoustic device and drawing it through the device; measuring an acoustic signal of the test sample as light from the lasers pass through the test sample; measuring the path-integrated extinction signal of each laser wavelength as the laser signal passes through the test sample; and determining the presence or absence of the chemical/biological agent of interest in the test sample.

One system embodiment, among others, comprises a photoacoustic device comprising a central hollow axial region configured to admit a gas at a first end and allow the gas to exit at a second end; a pump mounted to the second end of the central axial region, the pump adapted to pull the gas into the central axial region, through the central axial region, and out of the central axial region; at least two IR lasers located adjacent the central axial region, the lasers irradiating the central axial region with the light traveling from the laser through the central axial region; and a microphone mounted to an inner wall in the central hollow axial region, the microphone configured to detect an acoustic signal generated by absorption of the light by the particles in the gas, the acoustic signal proportional to the optical absorption by particles in the gas at the laser wavelengths of the light, and the microphone also configured to generate an electrical signal proportional to the acoustic signal.

Other devices, systems, methods, features, and advantages of the present disclosure will be or become apparent to one with skill in the art upon examination of the following drawings and detailed description. It is intended that all such additional devices, systems, methods, features, and advantages be included within this description and be within the scope of the disclosure.

BRIEF DESCRIPTION OF THE DRAWINGS

The components in the drawings are not necessarily to scale, emphasis instead being placed upon clearly illustrating the principles of the disclosed systems and methods.

Moreover, in the drawings, like reference numerals designate corresponding parts throughout the several views.

DETAILED DESCRIPTION

As will be described in detail here, photoacoustic-based devices, systems, and methods are provided. The photoacoustic-based devices are designed specifically for optical analysis of aerosols and generally include a windowless flow-through design. In particular, the photoacoustic devices and systems employ two or more infrared wavelengths, where the individual optical signals are deconvolved using a phase-sensitive detection scheme. By choosing wavelength values to coincide with absorption characteristics of a particular chemical/biological warfare agent, the photoacoustic device will function as an effective point sensor that is capable of detecting the presence of harmful chemical/biological aerosols.

Figure 1:
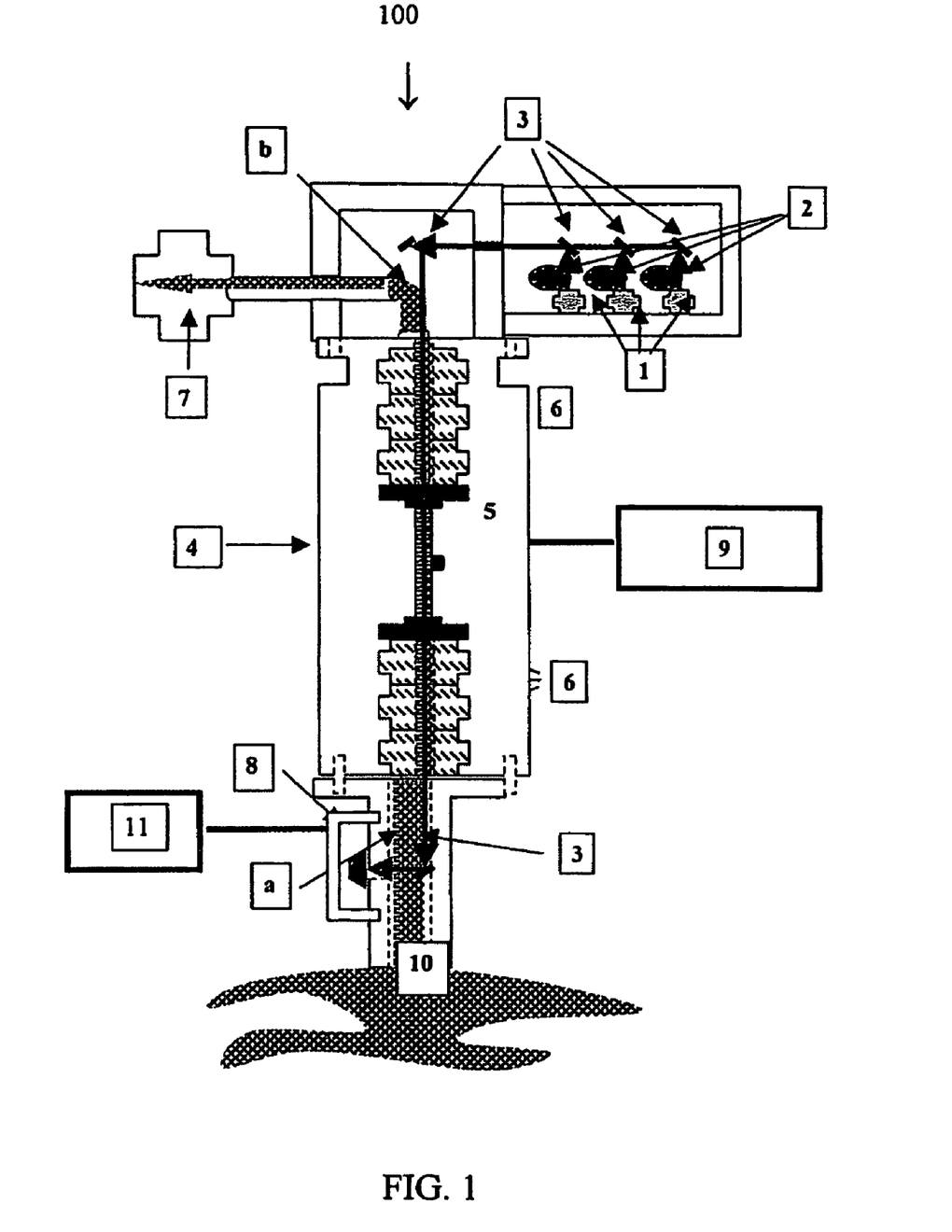
FIG. 1 is a schematic diagram of an embodiment of a disclosed photoacoustic device.

Having thus generally described the photoacoustic-based devices and systems, reference will now be made to the embodiments depicted in the drawings. FIG. 1 illustrates one embodiment of the disclosed photoacoustic devices, e.g., a multi-wavelength flow-through photoacoustic spectrophone 100. Included in the multi-wavelength spectrophone 100 is a modular set of two or more solid-state or gaseous based lasers 1 operating at different IR wavelengths, ($\lambda 1$, $\lambda 2$, $\lambda 3$, . . . $\lambda n$). With the advent of compact IR laser diode technology, e.g., quantum cascade laser diodes, a modular set of laser sources 1 (e.g., operating primarily in approximately the 2-14 µm wavelength range) can be employed in one embodiment where the lasers are configured to be interchangeable. Interchangeability of the set of lasers 1 allows for a choice of a particular wavelength set that may be desired to "tune" the photoacoustic device 100 for detection of a particular agent or group of agents. By operation in the mid- to long-wave IR region, the photoacoustic device 100 is configured to directly measure absorption bands that result from vibrational, rotational, and translational modes inherent in most complex organic and inorganic molecules.

The numerous laser signals can be deconvolved by modulating each source at different frequencies, ($\omega 1$, $\omega 2$, $\omega 3$, . . . $\omega n$), by employing various optical choppers 2. By modulating the different laser sources at different frequencies, a multi-channel lock-in amplifier 9 can separate the absorption response for each laser wavelength. Because the disclosed photoacoustic systems and methods employ multiple wavelength information, the ability to identify the presence of a particular airborne toxin or agent is greatly improved over a conventional single wavelength photoacoustic approach.

The IR laser beams are made coincident and directed through the spectrophone by a series of beam splitters and mirrors 3. Where desired, these optical elements can incorporate a fresh-air flush in order to keep the reflective surface(s) clean. The coincident lasers 1 are directed down through the center axial region of the spectrophone in which the aerosol/gas in question is drawn. The outer cylindrical cavity 4 of the spectrophone is machined from an acoustically dense material in order to suppress the ambient acoustic noise originating from the operational environment. For example, the outer cavity can be machined out of thick stainless steel or high density polyethylene. Further suppression of the ambient acoustic noise that can transverse down through the axial region of the spectrophone can be accomplished by the use of a series of acoustic dampeners 6 positioned above and below the photoacoustic active region.

Figure 2:
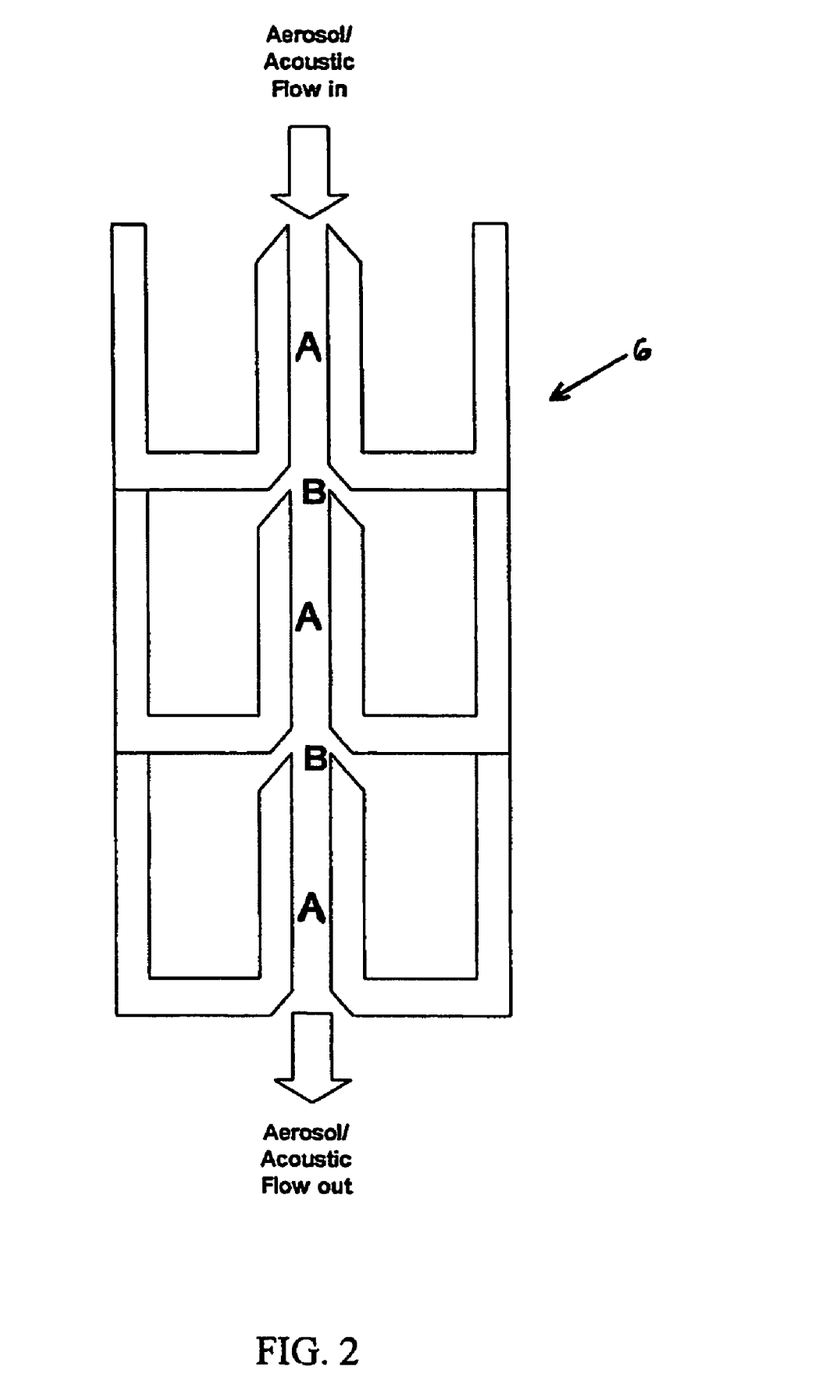
FIG. 2 is a schematic diagram of an embodiment of acoustic dampeners included in the photoacoustic device of FIG. 1.

Shown in FIG. 2 is a representation of an exploded cross-sectional schematic of the top set of three cylindrical dampeners 6 that fit within the spectrophone 100 and serve to dissipate acoustic noise that enters the spectrophone from the top opening. An identical set can also used at the bottom, as shown in the embodiment of FIG. 1, to suppress ambient noise originating from the bottom of the spectrophone. A simplified description of how the dampeners 6 operate is described as follows. Although the arrows in FIG. 2 demonstrate the aerosol and acoustic noise moving from top to bottom, one skilled in the art would understand the aerosol and acoustic noise movement can be in the opposite direction.

Both the aerosol and acoustic noise originating from the operating environment can flow freely through the center cylindrical region of the spectrophone 100. Acoustic noise that enters the spectrophone from the top and bottom of the flow-through design manifest themselves as pressure fluctuations radially distributed across the diameter of the column, e.g., point A of FIG. 2. The area at point A can be, for example, about 1.0 cm². As a pressure wave propagates down toward the inner cavity that houses the electret microphone 5 (FIG. 1), the pressure wave encounters one or more small apertures in the inlet column, depicted as points B in FIG. 2. At points B, the pressure wave is redistributed over a much larger area.

The larger redistribution area can be, for example, about 30.0 cm². Thus, the net pressure experienced across the spectrophone is effectively reduced. This reduction can be repeated at each aperture B until the desired noise reduction is achieved. For example, in one embodiment, a series of three or four dampeners 6 placed above and below the electret cavity are sufficient to suppress typical noise levels encountered in the laboratory. With the dampeners 6, a reduction of about 20 db is easily achieved at 1 kHz. Acoustic noise becomes an increasing problem at frequencies below about 100 Hz where acoustic filters become virtually impractical. Thus, in one embodiment the laser modulation frequency is greater than about 100 Hz. In one embodiment, the possible laser modulation frequencies range from approximately 200 to 10,000 Hz for desired noise suppression.

The test aerosol/gas 10 is drawn through the hollow axial region of the spectrophone by a pump located at the exit point 7. The modulated laser beam(s) is/are directed down through the well-defined column of aerosol/gas where a portion of the incident energy is absorbed. Because of the flow-through configuration of the photoacoustic device 100, problems previously associated with non-homogeneous aerosol concentrations are eliminated or reduced. The aerosol is more uniform due to the free-flowing nature of the media. In addition, because of the flow-through design, the sensitivity of the photoacoustic device 100 is not limited by residual absorption due to transmission windows.

The multi-wavelength absorption results in a multi-component acoustic signal that is detected by a small (for example, about 6 mm in diameter) highly sensitive electret microphone 5 that can be, in one embodiment, mounted to the wall of the inner cavity. The electret microphone 5 is externally powered through a simple resistor-capacitor (RC) circuit via a direct current (DC) power supply (not shown). The alternating current (AC) voltage(s) resulting from acoustic signal(s) can then be amplified and deconvolved using a first multi-channel lock-in amplifier 9 tuned to the modulation frequencies, ($\omega_1, \omega_2, \omega_3, \ldots \omega_n$). As noted previously, the acoustic signal(s) are proportional to the actual optical absorption at the laser wavelengths, ($\lambda_1, \lambda_2, \lambda_3, \ldots \lambda_n$), where the constant of proportionality is found via a calibration process.

The attenuated laser beam(s) are directed out of the spectrophone column via a reflective mirror 3 and are detected by an appropriate infrared (IR) optical detector 8. Again the resultant optical signal(s) can be amplified and deconvolved using a second tuned multi-channel lock-in amplifier 11. Because the primary electromagnetic interaction relied on is optical absorption, the detection signal is relatively insensitive to particle shape and/or size. As a result, the response of the device is far more stable than techniques that rely on optical scattering.

The proposed design includes a de facto short path transmissometer. This allows for an additional measure of the total absolute extinction. By taking the difference between the absorption and the total extinction, one can calculate an additional identifying parameter, e.g., the total scatter. By measuring changes in the laser beam('s)(s') attenuation and noting the extinction path length defined by points "a" and "b" of FIG. 1, the total extinction coefficient(s) for each wavelength considered can be calculated by applying Beers law.

Calibration of the flow-through photoacoustic spectrophone 100 can be accomplished by inserting an appropriate IR absorbing gas into the spectrophone cell. Typical gas/vapor used in prior single wavelength applications include isopropyl alcohol, methanol, and acetone.

The calibration gas is drawn through the system using the same flow dynamics and pump as described previously. A portion of the laser beam('s)(s') energy is absorbed by the gas, which results in a measurable extinction (measured by the detector 8) and absorption (detected by the electret microphone 5). Because the attenuating media is a gas, there is no scattering present and thus the extinction seen at the detector 8 for the path length defined by points a-b is equal to the measured optical absorption. The measured optical absorption is represented as an AC voltage from the electret microphone 5. The electret raw response in (mV) is converted to absolute, path integrated, absorption coefficients (1/m) via a simple Beers Law equation.

The set of the resultant spectral absorption $\{\alpha(\lambda_1), \alpha(\lambda_2), \ldots \alpha(\lambda_n)\}$, and extinction, $\{\epsilon(\lambda_1), \epsilon(\lambda_2), \ldots \epsilon(\lambda_n)\}$, form a uniquely identifiable series of parameters that are associated with a particular chemical/biological warfare agent in question.

EXAMPLE

Having described an exemplary embodiment of the disclosed aerosol photoacoustic device with respect to FIGS. 1 and 2, given below is an example of the photoacoustic device in practice.

A preferred embodiment for of the photoacoustic device includes the following: 1) two or more modulated, monochromatic, IR sources of radiation; 2) an acoustically isolated region within the spectrophone that houses a sensitive electret microphone; 3) a short-path transmissometer configured to accurately measure the total optical extinction; and 4) a phase sensitive detection set of electronics appropriate to amplify and deconvolve the individual response from multiple excitation wavelengths.

Figure 3:
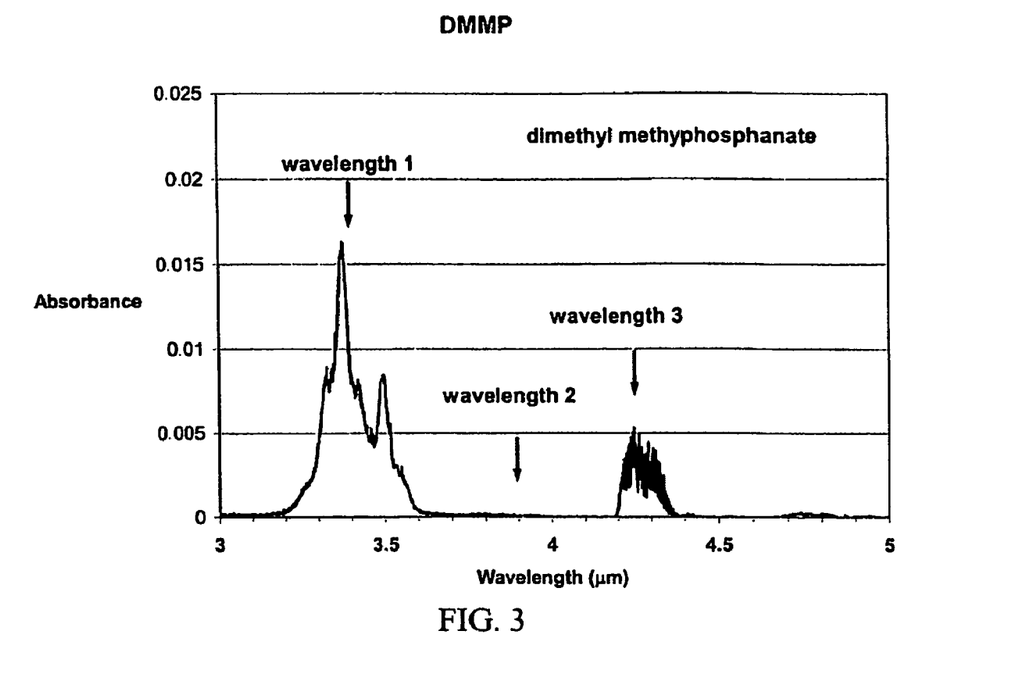
FIG. 3 is a graph illustrating an IR spectra of dimethyl methylphosphanate, an agent that can be detected by the photoacoustic device of FIG. 1.

An exemplary application of the disclosed photoacoustic device includes detecting/identifying an airborne chemical toxin. For example, the IR absorption spectra for the chemical warfare simulant, dimethyl methylphosphanate, (DMMP), is shown in FIG. 3. In order to detect the presence of DMMP, the flow-through photoacoustic device 100 is configured with three laser diode modules 1, each laser operating at one of the identified three wavelengths shown in FIG. 3. Each laser is modulated at the frequency, $\omega_1, \omega_2$, or $\omega_3$.

For example, the laser can be modulated using an optical modulator/chopper 2. For DMMP, two wavelengths are chosen that are on two absorption bands and one wavelength of any absorption. If the spectrophone 100 draws in a sample of the air/toxin mixture 10, the wavelengths labeled 1 and 3 seen in the DMMP spectra will be partially absorbed by the toxin, resulting in a proportional acoustic signal(s).

Resultant AC signals are recorded by a multi-channel lock-in amplifier 9, tuned to detect only signals modulated at $\omega 1$, $\omega 2$, and $\omega 3$ and are then converted to the absorption coefficients $\alpha(\omega 1)$, $\alpha(\omega 2)$, and $\alpha(\omega 3)$. Additionally, the resultant path integrated extinction for each laser wavelength is detected in a similar fashion using phase sensitive detection, e.g., $\epsilon(\omega 1)$, $\epsilon(\omega 2)$, and $\epsilon(\omega 3)$. These six independent, spectrally resolved parameters represent a measure of the total extinction, $\epsilon(\omega 1)$, $\epsilon(\omega 2)$, $\epsilon(\omega 3)$ and absorption, $\alpha(\omega 1)$, $\alpha(\omega 2)$, and $\alpha(\omega 3)$, and, as such, form a unique set of parameters that can be used to signify the presence and concentration of the chemical warfare simulant, DMMP.

Figure 4A:
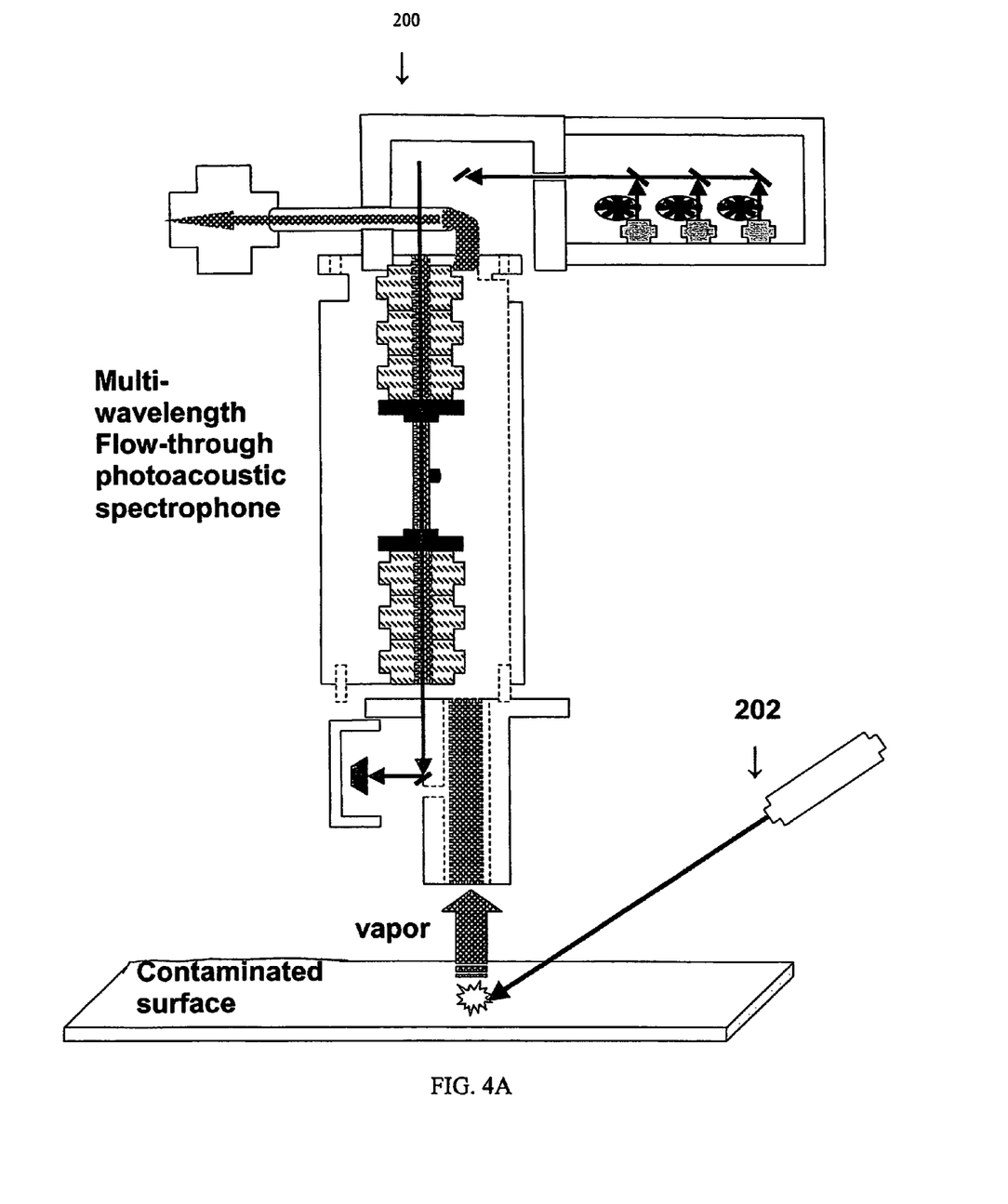
FIG. 4A is a schematic diagram that illustrates an embodiment of an exemplary photoacoustic system.
Figure 4B:
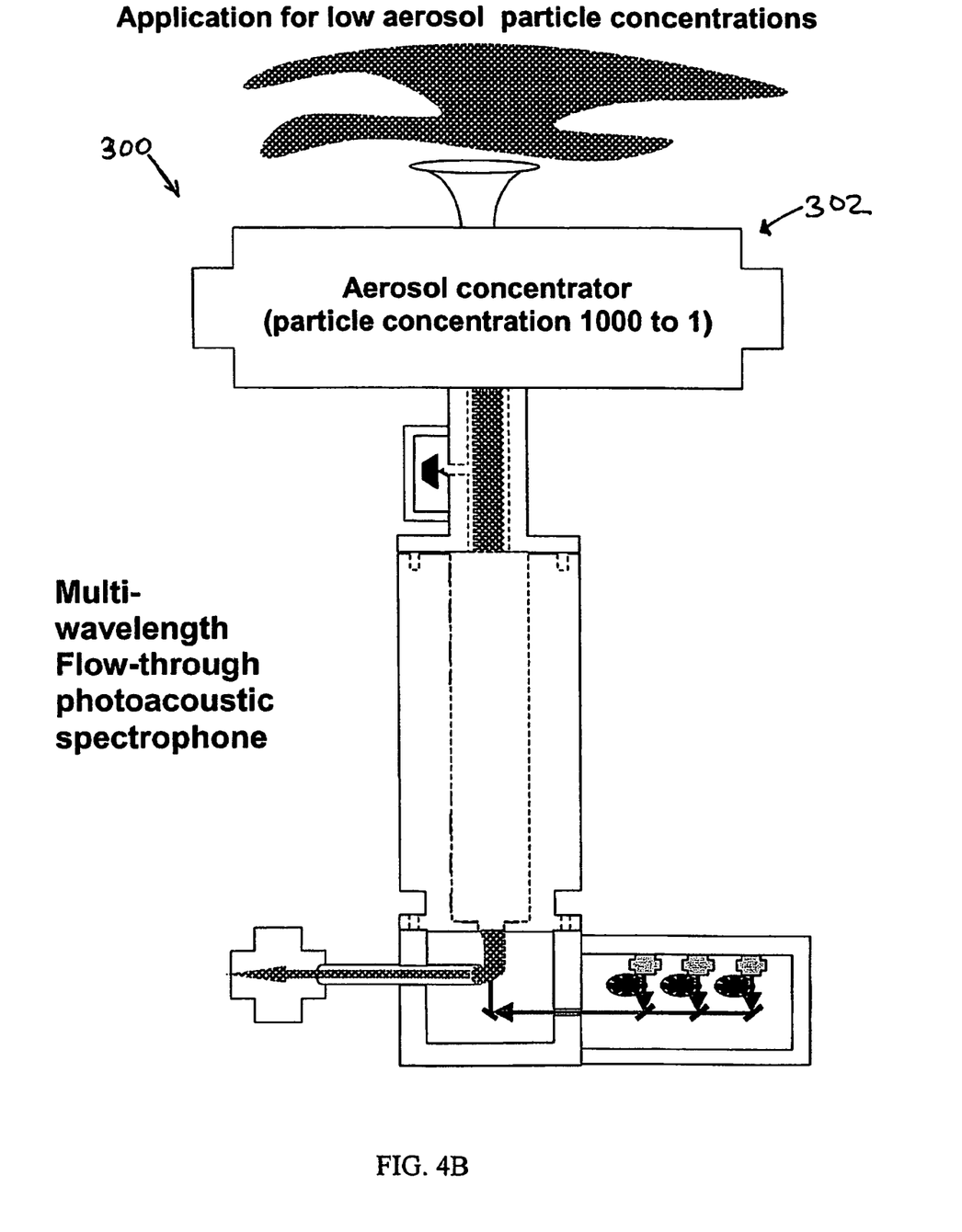
FIG. 4B is a schematic diagram that illustrates an embodiment of an exemplary photoacoustic system.

The utility of the flow-through photoacoustic device 100 can be expanded by incorporating additional instrumentation, see FIGS. 4A and 4B. FIG. 4A illustrates an exemplary configuration of a photoacoustic system 200 in which an external laser source 202 is used to heat a particular bulk sample, e.g., a contaminated surface, in order to form a chemical vapor that is then sampled by the spectrophone. By configuring the proposed flow-through photoacoustic device with an external means for heating of a bulk sample, e.g., a laser, the photoacoustic system 200 can detect trace chemical and/or biological contaminates on any macroscopic surfaces, e.g., vehicles, buildings, furniture, soil, etc.

To improve S/N ratio when operating at ambient conditions, a commercially available aerosol concentrator 302 could be fashioned to the input of the photoacoustic spectrophone system 300 illustrated in FIG. 4B. The concentrator 302 effectively increases the number of aerosol particle per unit volume and improves the spectrophone's sensitivity when sampling very low concentrations of a chemical/biological agent.

Figure 5:
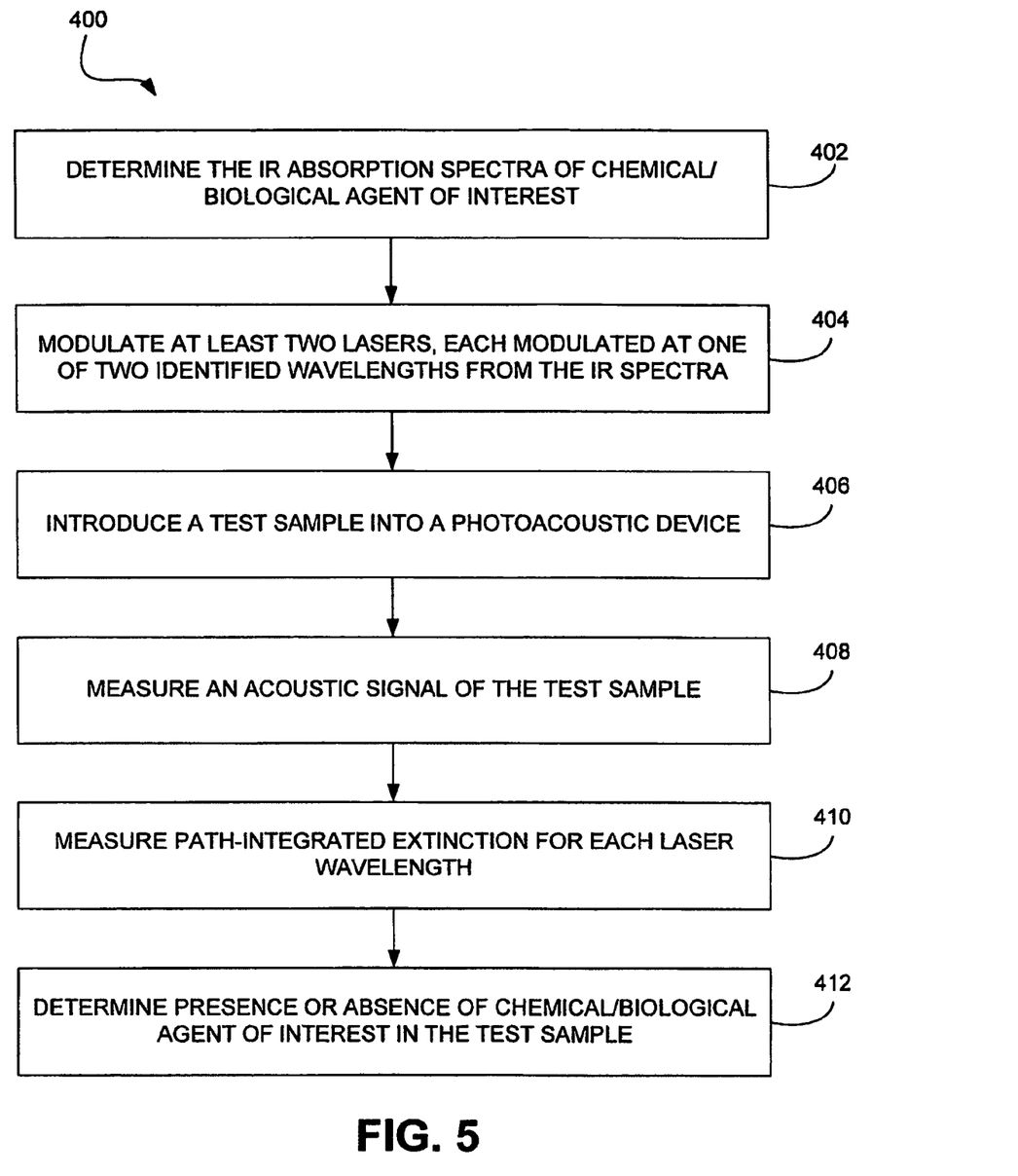
FIG. 5 is a flow diagram that illustrates an embodiment of a photoacoustic method.

In view of the above description, it will be appreciated that one embodiment of a photoacoustic method 400 may include, as illustrated in FIG. 5, determining the IR absorption spectra of a chemical/biological agent of interest (402), modulating at least two lasers in a photoacoustic device, each modulated laser operating at one of two identified wavelengths from the IR spectra (404), introducing a test sample into the photoacoustic device (406) and drawing it through the device, measuring an acoustic signal of the test sample as the laser passes through the test sample (408), measuring the path-integrated extinction signal of each laser wavelength as the laser signal passes through the test sample (410), and determining the presence or absence of the chemical/biological agent of interest in the test sample (412).

Any process descriptions or blocks in the flow diagrams as described in FIG. 5 should be understood as representing steps in the process, and alternate implementations are included within the scope of the preferred embodiments, in which functions can be executed out of order from that shown or discussed, including substantially concurrently or in reverse order, depending on the functionality involved, as would be understood by those reasonably skilled in the art.

It should be emphasized that the above-described embodiments of the present disclosure, particularly, any "preferred" embodiments, are merely possible examples of implementations, merely set forth for a clear understanding of the principles of the disclosed systems and methods. Many variations and modifications can be made to the above-described embodiment(s) without departing substantially from the principles of the systems and methods. All such modifications and variations are intended to be included herein within the scope of this disclosure.

The invention claimed is:

1. A photoacoustic system comprising:
a photoacoustic device comprising
a central hollow axial region configured to admit a gas at a first end and allow the gas to exit at a second end;
a pump mounted to the second end of the central axial region, the pump adapted to pull the gas into the central axial region, through the central axial region, and out of the central axial region;
at least two infrared (IR) lasers located adjacent the central axial region, the lasers irradiating the central axial region with the light traveling from the laser through the central axial region; and
a microphone mounted to an inner wall in the central hollow axial region, the microphone configured to
detect an acoustic signal generated by absorption of the light by the particles in the gas, the acoustic signal proportional to the optical absorption by particles in the gas at the laser wavelengths of the light, and
generate an electrical signal proportional to the acoustic signal.

2. The system of claim 1, further comprising choppers configured to modulate the IR lasers at different frequencies.

3. The system of claim 1, wherein IR lasers operate at different wavelengths.

4. The system of claim 3, wherein IR lasers operate in approximately 2-14 μm wavelength range.

5. The system of claim 1, wherein IR lasers are configured to be interchangeable to allow for a particular wavelength set to "tune" the photoacoustic device for detection of a particular agent in the gas.

6. The system of claim 1, further comprising a multi-channel lock-in amplifier configured to separate an absorption response of each laser wavelength.

7. The system of claim 1, further comprising an acoustic dampener.

8. The system of claim 1, further comprising a series of acoustic dampeners positioned on either end of an active region of the axial region.

9. The system of claim 1, further comprising a series of acoustic dampeners positioned on either end of an active region of the axial region, the dampeners comprising
a column configured to admit a gas at a first end and allow the gas to exit at a second end; and
an aperture in the column leading to an area that has a larger surface area than the column.

10. The system of claim 1, wherein the microphone is an electret microphone.

11. The system of claim 1 further comprising:
an IR optical detector adjacent the first end; and
a multi-channel lock-in amplifier adjacent the IR optical detector, the amplifier configured to amplify and deconvolve a resultant optical signal.

12. The system of claim 1, further comprising a laser source external to the device, the laser source configured to heat a bulk sample to produce the gas.

13. The system of claim 1, further comprising an aerosol concentrator fashioned at the second end of the axial region.

14. A system for detecting the presence or absence of a particular chemical or biological agent comprising:

means for modulating at least two lasers in a photoacoustic device, whereby each modulated laser operates at one of at least two identified wavelengths from the IR spectra;

means for drawing the test sample into, through, and out of the system;

means for measuring an acoustic signal of the test sample as light from the lasers pass through the test sample; and means for measuring the path-integrated extinction signal of each laser wavelength as the laser signal passes through the test sample.

15. A method of detecting the presence or absence of a chemical/biological agent in a test sample comprising the steps of:

determining a spectrum of infrared (IR) absorption bands characteristic of the chemical/biological agent;

selecting two or more light wavelengths from the spectrum of infrared (IR) absorption bands and determining acoustic signal and a path-integrated extinction signal characteristic responses of the chemical/biological agent to the light wavelengths;

modulating each light beam of the selected wavelength and passing the modulated light beams through the test sample:
(a) measuring an acoustic signal emitted by the test sample in response to the modulated light beams, and
(b) measuring a path-integrated extinction signal of each modulated light beam in the test sample; and determining the presence or absence of the chemical/biological agent in the test sample by comparison of the measurements with the characteristic responses and giving an indication thereof.

16. The method of claim 15, wherein modulating is at a frequency greater than about 100 Hz.

17. The method of claim 15, wherein modulating is at a frequency of about 200 to 10,000 Hz.

18. The method of claim 15, wherein each light beam is modulated at a different frequency.

19. The method of claim 15, wherein measuring the acoustic signal emitted by the test sample comprises:
detecting the acoustic signal and
generating an electrical signal proportional to the acoustic signal.

20. The method of claim 15, wherein measuring the acoustic signal emitted by the test sample comprises:
detecting the acoustic signal;
generating an electrical signal proportional to the acoustic signal; and
deconvolving the electrical signal.

21. The method of claim 15, wherein measuring the coustic signal emitted by the test sample comprises:
modulating each light beam at a different frequency;
generating a multi-component acoustic signal in the test sample by passing the modulated light beams through the test sample;
generating an electrical signal proportional to the multi-component acoustic signal; and
deconvolving the electrical signal.

* * * * *